(12) United States Patent
Hudson

(10) Patent No.: US 6,193,511 B1
(45) Date of Patent: Feb. 27, 2001

(54) APPARATUS AND METHOD FOR CLEANING DENTAL ARTICULATORS

(76) Inventor: Alan P. Hudson, 105 Muse St., Jackson, TN (US) 38301

(*) Notice: Subject to any disclaimer, the term of this patent is extended or adjusted under 35 U.S.C. 154(b) by 0 days.

(21) Appl. No.: 09/534,764

(22) Filed: Mar. 24, 2000

(51) Int. Cl.$^7$ .................................................. A61C 11/00
(52) U.S. Cl. ................................................. 433/54; 433/60
(58) Field of Search .......................................... 433/54–74

(56) References Cited

U.S. PATENT DOCUMENTS

| | | | |
|---|---|---|---|
| Re. 31,476 | 12/1983 | Mercer | 264/16 |
| 2,483,094 | 9/1949 | Harvey | 18/42 |
| 4,481,162 | 11/1984 | Huffman | 264/334 |
| 5,403,185 | 4/1995 | Presswood | 433/74 |
| 5,466,152 | 11/1995 | Walter | 433/60 |
| 5,569,033 | 10/1996 | Michael | 433/74 |
| 5,580,244 | * 12/1996 | White | 433/37 |
| 5,658,143 | 8/1997 | Kuperman | 433/60 |

\* cited by examiner

*Primary Examiner*—Nicholas D. Lucchesi
(74) *Attorney, Agent, or Firm*—Walker, McKenzie & Walker, P.C.

(57) ABSTRACT

An apparatus and method for cleaning a dental articulator of the type including a body member having a plurality of precisely spaced holes extending therethrough. The apparatus including a base; and a plurality of precisely spaced pins extending from the base for insertion into the plurality of precisely spaced holes in the body member of the dental articulator to clean any debris from the plurality of precisely spaced holes in the body member of the dental articulator. The pins of the apparatus have the same precise spacing as the precisely spaced holes extending through the body member of the articulator and being sized to be inserted into and through the precisely spaced holes extending through the body member of the articulator. The method includes the step of forcing the pins of the apparatus through the precisely spaced holes extending through the body member of the articulator.

9 Claims, 3 Drawing Sheets

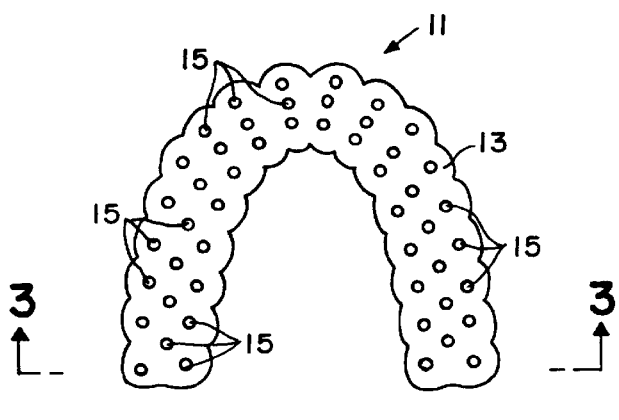
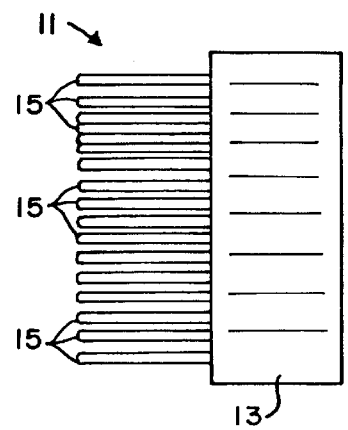
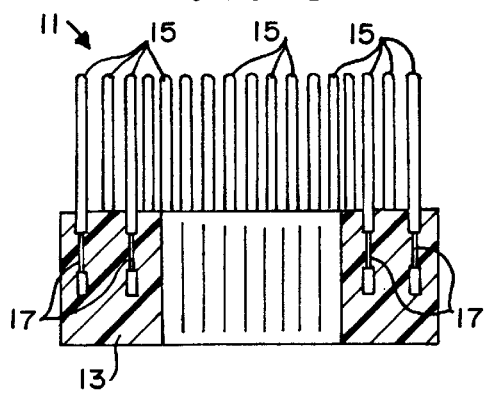
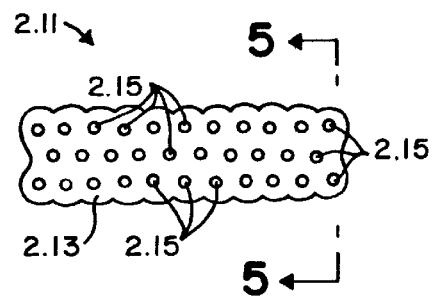
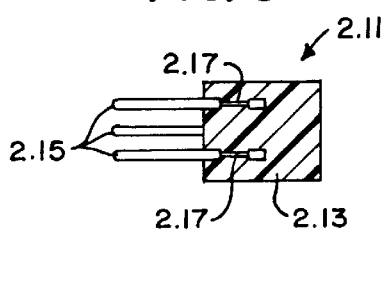
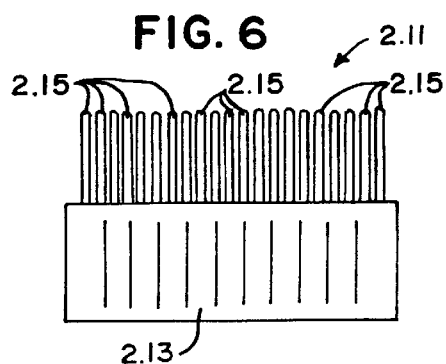

APPARATUS AND METHOD FOR CLEANING DENTAL ARTICULATORS

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to dental articulators and, more specifically, to an apparatus for cleaning casting material from such dental articulators after the dental articulators have been used in the fabrication of dental models (e.g., prosthetic crowns, bridges, partials, dentures, etc.).

2. Information Disclosure Statement

A dental articulator simulates the movement of a human jaw, and numerous dental articulators have been developed to articulate or mount together the upper and lower dental casts of a patient's teeth or edentulous arches in the same centric relationship as they interdigitate or come together in the mouth for use by dentists and/or dental technicians in the fabrication of dental prosthetic crowns, bridges, partials, dentures, etc. Many such dental articulators have built into them the ability for the dentist or dental technician to duplicate the lateral and protrusive excurtion movements that occur during maxification.

A preliminary patentability search conducted in class 433, subclasses 60, 74, 213, 42, and in class 249, subclasses 54, 67 and 68 produced the following patents which appear to be relevant to the present invention:

Harvey, U.S. Pat. No. 2,483,094, discloses a stripping and knockout mechanism for molding dies of the type that are customarily employed in connection with injection molding machines.

Huffman, U.S. Pat. No. 4,481,162, issued Nov. 6, 1984, discloses a flexible mold for use with a dental articulator. The flexible mold defines either a full base or a quadrant base of a dental model, and includes a perimeter member for defining the side walls of the base and a shelf extending inwardly from the rear side wall for delineating a slot at the rear of the base. The slot allows one arm of an articulator to be attached to one base and the other arm of the articulator to be attached to an opposing base.

Presswood, U.S. Pat. No. 5,403,185, issued Apr. 4, 1995, discloses a dental articulator including first and second trays hingedly secured to allow articulating movement of the trays with respect to each other with at least one of the trays provided with a grid having a plurality of holes in a spaced pattern to receive pins for supporting a dental prosthetic model.

Walter, U.S. Pat. No. 5,466,152, issued Nov. 14, 1995, discloses a dental articulator for creating a pinned model of a patient's mandibular and maxillary dental arches. The articulator includes recessed maxillary and mandibular tray support members, each containing a plurality of indexing holes into which indexing pins can be inserted.

Kuperman, U.S. Pat. No. 5,658,143, issued Aug. 19, 1997, discloses a dental articulator including upper and lower arches, each for receiving a dental cast of teeth and each having a grid pattern that includes a plurality of dowel pin holes that define multiple dowel pin locations for receiving a plurality of dowel pins, and a plurality of support pin holes that define multiple pin locations for receiving a plurality of support pins. The dowel pin and support pin locations are spaced apart such that a die may be held in place within the upper and lower arches by a plurality of dowel pins and by a plurality of support pins to prevent movement or rotation of the individual die or dies.

Michael, U.S. Pat. No. 5,569,033, issued Oct. 29, 1996, discloses a dental die model (i.e., a positive molding of teeth and associated gum area) for use with or without articulating devices.

Mercer, U.S. Pat. No. Re. 31,476, reissued Dec. 27, 1983, discloses a cast ejector for use in removing a master dental cast from a impression material-containing, duplication flask.

During the typical fabrication of dental models using dental articulators of the type disclosed in Walter, U.S. Pat. No. 5,466,152, and Kuperman, U.S. Pat. No. 5,658,143, casting material (e.g., a gypsum material often referred to as dental stone) will normally become embedded in one or more of the holes or channels. While such articulators have been soaked in a solution of acetone (solvent) for 48–72 hours to remove the embedded casting material, etc., the time and work involved in such cleaning operations and the known dangers in working with such chemicals, have limited its use and such articulators are frequently advertised and sold to be used only one time.

Nothing in the known prior art discloses or suggests the present invention. More specifically, nothing in the known prior art discloses or suggests an apparatus for cleaning a dental articulator including a base, and a plurality of precisely spaced pins extending from the base for insertion into the plurality of precisely spaced holes in the body member of a dental articulator to clean any debris from the plurality of precisely spaced holes in the body member of the dental articulator; the pins having the same precise spacing as the precisely spaced holes extending through the body member of the articulator and being sized to be inserted into and through the precisely spaced holes extending through the body member of the articulator.

BRIEF SUMMARY OF THE INVENTION

The present invention provides an apparatus for cleaning a dental articulator. A basic concept of the present invention is to provide an apparatus having means for being forced through the plurality of precisely spaced holes in the body member of a dental articulator to clean any debris (e.g., embedded plugs of casting material) from the plurality of precisely spaced holes in the body member of the dental articulator.

The apparatus of the present invention comprises, in general, a base, and a plurality of precisely spaced pins extending from the base for insertion into the plurality of precisely spaced holes in the body member of a dental articulator to clean any debris from the plurality of precisely spaced holes in the body member of the dental articulator; the pins having the same precise spacing as the precisely spaced holes extending through the body member of the articulator and being sized to be inserted into and through the precisely spaced holes extending through the body member of the articulator.

BRIEF DESCRIPTION OF THE SEVERAL VIEWS OF THE DRAWINGS

FIG. 1 is a top plan view of a first preferred embodiment of the apparatus for cleaning dental articulator devices of the present invention.

FIG. 2 is a side elevational view of the apparatus of FIG. 1.

FIG. 3 is a sectional view substantially as taken on line 3—3 of FIG. 1 with portions thereof broken away or omitted for clarity.

FIG. 4 is a top plan view of a second preferred embodiment of the apparatus for cleaning dental articulator devices of the present invention.

FIG. 5 is a sectional view substantially as taken on line 5—5 of FIG. 4 with portions thereof broken away or omitted for clarity.

FIG. 6 is a side elevational view of the apparatus of FIG. 4.

DETAILED DESCRIPTION OF THE INVENTION

Figure 7:
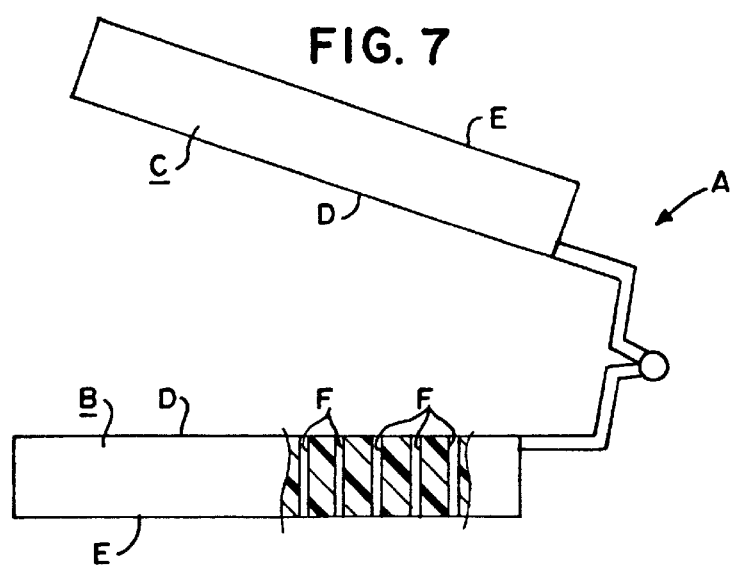
FIG. 7 is a side elevational view of a common prior art dental articulator with portions thereof broken away for clarity.
Figure 8:
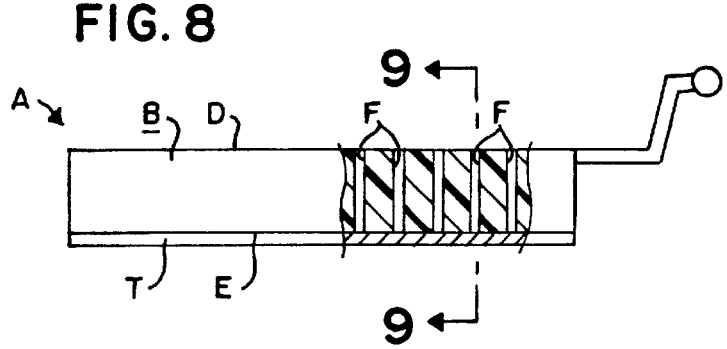
FIG. 8 is a side elevational view of a portion of the dental articulator of FIG. 7, showing tape applied to a surface of the body member of the dental articulator in a step of a method of using the apparatus of the present invention to clean a dental articulator.
Figure 9:
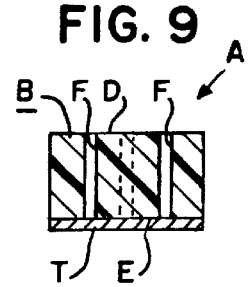
FIG. 9 is a sectional view as taken on line 9—9 of FIG. 8.
Figure 10:
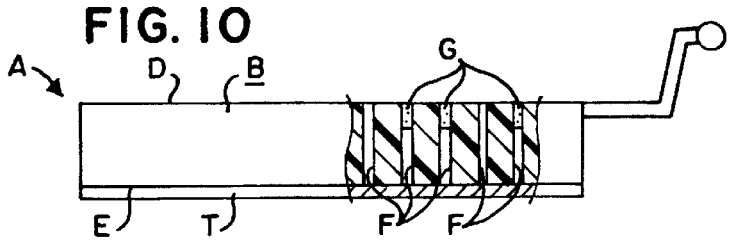
FIG. 10 is a side elevational view similar to FIG. 8 but showing casting material casting material embedded within certain of the holes extending through the body member of the dental articulator after the dental articulator has been used in the fabrication of a dental model.
Figure 11:
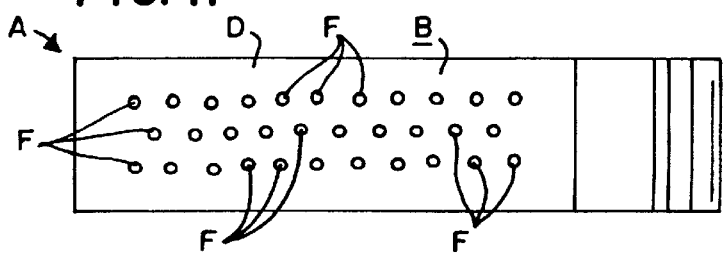
FIG. 11 is a top plan view of FIG. 10.
Figure 12:
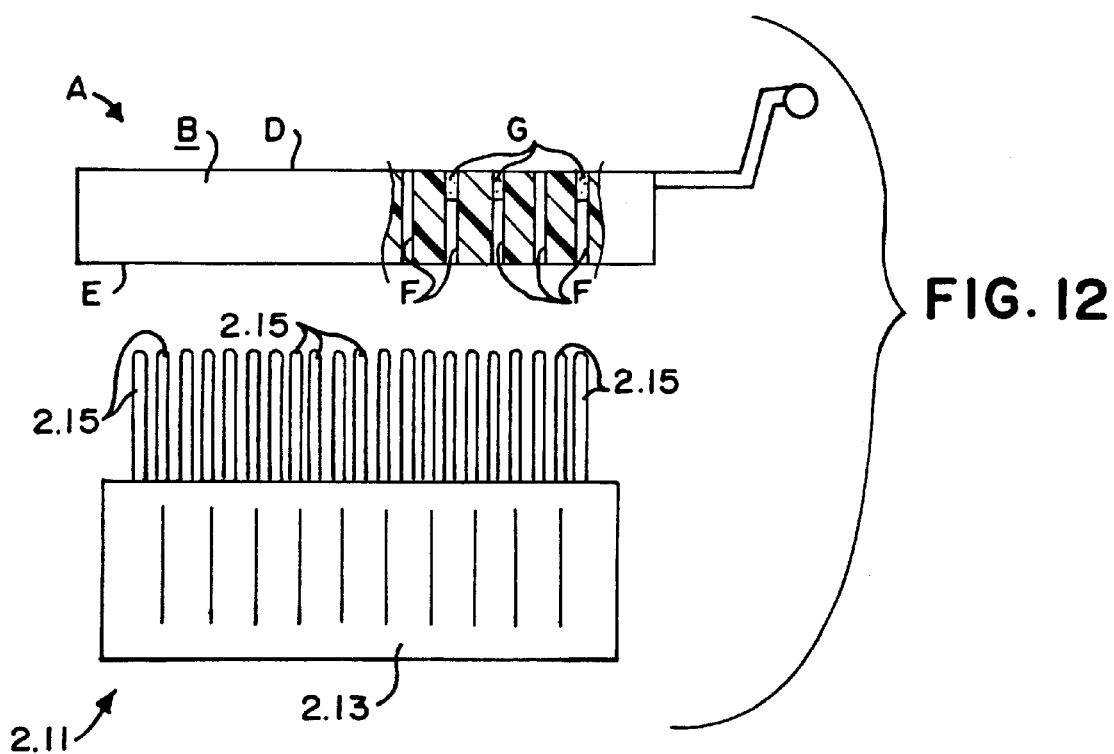
FIG. 12 is a side elevational view similar to FIG. 10 but showing the tape removed from the body member of the dental articulator and showing the apparatus of FIG. 4 being brought into position with respect to the body member of the dental articulator in a step of a method of using the apparatus of the present invention to clean a dental articulator.
Figure 13:
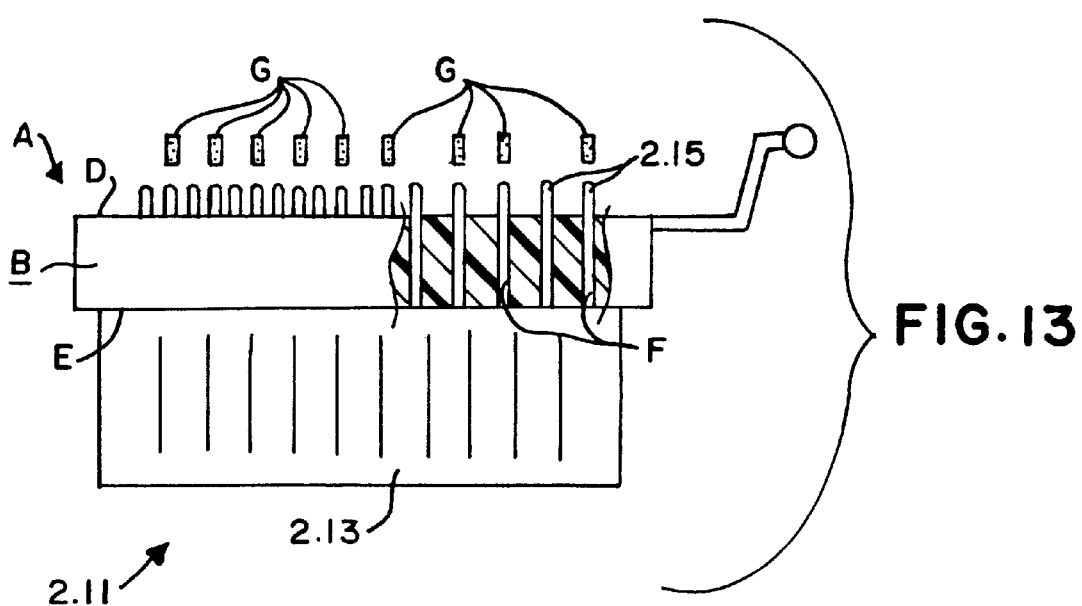
FIG. 13 is a side elevational view similar to FIG. 12 but showing the precisely spaced pins of the apparatus of FIG. 4 inserted completely through the precisely spaced holes of the dental articulator, causing the casting material embedded in those holes to be ejected from the dental articulator.

A first preferred embodiment of the cleaning apparatus of the present invention is shown in FIGS. 1–3, and identified by the numeral 11. A second preferred embodiment of the cleaning apparatus of the present invention is shown in FIGS. 4–6, 12 and 13, and identified by the numeral 2.11. Both cleaning apparatuses 11, 2.11 are designed for use with typical prior art dental articulators such as the dental articulator disclosed by Kuperman, U.S. Pat. No. 5,658,143, issued Aug. 19, 1997, and the dental articulator disclosed by Walter, U.S. Pat. No. 5,466,152, issued Nov. 14, 1995, both of which being incorporated herein by reference. A typical prior art dental articulator is shown in FIGS. 7–13, and identified by the reference character A. The articulator A includes a first body member B and a second body member C hinged or articulating joined together. The body members B, C may be substantially mirror images of one another, having a first surface D, a second surface E, and a plurality of precisely spaced holes F extending therethrough between the first and second surfaces D, F. During the fabrication of dental models using the dental articulator A, plugs G of casting material (e.g., a gypsum material often referred to as dental stone) will often become embedded in one or more of the holes F as clearly shown in FIG. 12.

The cleaning apparatus 11 includes a base 13, and a plurality of precisely spaced pins 15 extending from the base 13 for insertion into the plurality of precisely spaced holes F in a body member B, C of a dental articulator A to clean any debris (I.e., embedded plugs G of casting material) from the plurality of precisely spaced holes F in the body member B, C of the dental articulator A.

The base 13 may be arcuate shaped as shown in FIG. 1, sized to approximate an arcuate shaped die-receiving surface of a body member B, C of a arch-type dental articulator A such as the U-shaped upper or lower arch 12, 14 of the dental articulator 10 disclosed in the above incorporated and cited Kuperman patent (U.S. Pat. No. 5,658,143). On the other hand, the base 13 may be of any other shape large enough to allow an arcuate shaped grid or layout of precisely spaced pins 15 to extend therefrom. The base 13 may be constructed out of any substantially strong material. The base 13 may be molded or otherwise constructed out of a plastic, preferably polyurethane.

The pins 15 have the same precise spacing as the precisely spaced holes F extending through the body member B, C of an articulator A to be cleaned, and are sized to be inserted into and through the precisely spaced holes F extending through the body member B, C of the articulator A. The pins 15 are constructed out of a strong material such as metal, and are preferably cut from an elongated length of stainless steel, e.g., type 302 spring temper stainless steel, having a diameter of 1 millimeter and an overall length of 17 millimeters so that 5 millimeters of one end portion thereof can be embedded or molded into the base 13, leaving 12 millimeters to be inserted into and through one of the precisely spaced holes F extending through the body member B, C of the articulator A. A notch 17 may be rolled or otherwise formed into each pin 15 approximately midway of the end portion thereof to be embedded or molded into the base 13 to help hold and anchor each pin 15 to the base 13. The edge or corner of at least the outer end of each pin 15 (i.e., the end thereof to be inserted into one of the precisely spaced holes F extending through the body member B, C of the articulator A) is preferably slightly rounded.

The cleaning apparatus 2.11 includes a base 2.13, and a plurality of precisely spaced pins 2.15 extending from the base 2.13 for insertion into the plurality of precisely spaced holes F in a body member B, C of a dental articulator A to clean any debris from the plurality of precisely spaced holes F in the body member B, C of the dental articulator A.

The base 2.13 may have an elongate, generally rectangular shape as shown in FIG. 4, sized to approximate a rectangular shaped die-receiving surface of a body member B, C of a arch-type dental articulator A such as the rectangular-shaped upper or lower arch 212, 214 of the dental articulator 200 disclosed in the above incorporated and cited Kuperman patent (U.S. Pat. No. 5,658,143). On the other hand, the base 2.13 may be of any other shape large enough to allow an rectangular shaped grid or layout of precisely spaced pins 2.15 to extend therefrom. The base 2.13 may be constructed out of any substantially strong material. The base 2.13 may be molded or otherwise constructed out of a plastic, preferably polyurethane.

The pins 2.15 have the same precise spacing as the precisely spaced holes F extending through the body member B, C of an articulator A to be cleaned, and are sized to be inserted into and through the precisely spaced holes F extending through the body member B, C of the articulator A. The pins 2.15 are constructed out of a strong material such as metal, and are preferably cut from an elongated length of stainless steel, e.g., type 302 spring temper stainless steel, having a diameter of 1 millimeter and an overall length of 17 millimeters so that 5 millimeters of one end portion thereof can be embedded or molded into the base 2.13, leaving 12 millimeters to be inserted into and through one of the precisely spaced holes F extending through the body member B, C of the articulator A. A notch 2.17 may be rolled or otherwise formed into each pin 2.15 approximately midway of the end portion thereof to be embedded or molded into the base 2.13 to help hold and anchor each pin 2.15 to the base 13. The edge or corner of at least the outer end of each pin 2.15 (i.e., the end thereof to be inserted into one of the precisely spaced holes F extending through the body member B, C of the articulator A) is preferably slightly rounded.

The method of using and cleaning a dental articulator of the present invention comprising the steps of first applying tape T to the second surface E of the body member B, C of the dental articulator A (see FIGS. 8–10), then creating a dental model using a typical casting material on the first surface D of the body member B, C of the dental articulator A; then removing the dental model from the first surface D of the body member B, C of the dental articulator A; then removing the tape T from the second surface E of the body member B, C of the dental articulator A; and then inserting the precisely spaced pins 15, 2.15 of the cleaning apparatus 11, 2.15 into the precisely spaced holes F in the second surface E of the body member B, C of the articulator A and forcing the precisely spaced pins 15, 2.15 of the cleaning apparatus 11, 2.15 completely through the precisely spaced holes F in the second surface E of the body member B, C of the articulator A to eject or force any plugs G of casting material out of the precisely spaced holes F in the second surface E of the body member B, C of the articulator A (see FIGS. 12 and 13) that may have entered one or more of the precisely spaced holes F in the second surface E of the body member B, C of the articulator A during the dental model creating step.

Although the present invention has been described and illustrated with respect to preferred embodiments and a preferred use therefor, it is not to be so limited since modifications and changes can be made therein which are within the full intended scope of the invention.

What is claimed is:

1. An apparatus for cleaning a dental articulator of the type including a body member having a plurality of precisely spaced holes extending therethrough; said apparatus comprising:

(a) a base; and (b) a plurality of precisely spaced pins extending from said base for insertion into the plurality of precisely spaced holes in the body member of the dental articulator to clean any debris from the plurality of precisely spaced holes in the body member of the dental articulator; said pins having the same precise spacing as the precisely spaced holes extending through the body member of the articulator and being sized to be inserted into and through the precisely spaced holes extending through the body member of the articulator.

2. The apparatus of claim 1 in which said base is elongated.

3. The apparatus of claim 1 in which said based is arcuate.

4. The apparatus of claim 1 in which said pins are metal.

5. The apparatus of claim 4 in which said pins are stainless steel.

6. The apparatus of claim 1 in which said base is plastic.

7. The apparatus of claim 6 in which said base is polyurethane.

8. An apparatus for cleaning a dental articulator of the type including a body member having a first surface and a second surface, and having a plurality of precisely spaced holes extending therethrough between the first and second surfaces; said apparatus comprising:

(a) a base; and (b) a plurality of precisely spaced pins extending from said base a distance at least equal to the distance between the top and bottom surfaces of the body member of the dental articulator for insertion through the plurality of precisely spaced holes in the body member of the dental articulator to clean any debris from the plurality of precisely spaced holes in the body member of the dental articulator; said pins having the same precise spacing as the precisely spaced holes extending through the body member of the articulator and being sized to be inserted into and through the precisely spaced holes extending through the body member of the articulator.

9. A method of using and cleaning a dental articulator of the type including a body member having a first surface and a second surface opposing the first surface, and having a plurality of precisely spaced holes extending therethrough between the first and second surfaces, said method comprising the steps of:

(a) applying tape to the second surface of the body member of the dental articulator; then (b) creating a dental model using a casting material on the first surface of the body member of the dental articulator; then (c) removing the dental model from the first surface of the body member of the dental articulator; then (d) removing the tape from the second surface of the body member of the dental articulator;

(e) providing a cleaning apparatus including a base and a plurality of precisely spaced pins extending from the base, the pins having the same precise spacing as the precisely spaced holes extending through the body member of the articulator and being sized to be inserted into and completely through the precisely spaced holes extending through the body member of the articulator; and then (f) inserting the precisely spaced pins of the cleaning apparatus into the precisely spaced holes in the second surface of the body member of the articulator and forcing the precisely spaced pins of the cleaning apparatus completely through the precisely spaced holes in the body member of the articulator to force out of the precisely spaced holes in the body member of the articulator any casting material that may have entered one or more of the precisely spaced holes in the body member of the articulator during the dental model creating step.

* * * * *